United States Patent
Feldmann et al.

(10) Patent No.: US 7,599,747 B2
(45) Date of Patent: Oct. 6, 2009

(54) SCREW-IN ELECTRODE PROBE FOR CARDIOLOGOCAL APPLICATION

(75) Inventors: Jörg Feldmann, Berlin (DE); Gernot Kolberg, Berlin (DE); Hartmut Lenski, Glienicke (DE)

(73) Assignee: Biotronik CRM Patent AG (CH)

( * ) Notice: Subject to any disclaimer, the term of this patent is extended or adjusted under 35 U.S.C. 154(b) by 469 days.

(21) Appl. No.: 11/464,635

(22) Filed: Aug. 15, 2006

(65) Prior Publication Data
US 2007/0055335 A1    Mar. 8, 2007

(30) Foreign Application Priority Data
Sep. 7, 2005    (DE) .................. 10 2005 042369

(51) Int. Cl.
*A61N 1/00*    (2006.01)
(52) U.S. Cl. ...................................... 607/127
(58) Field of Classification Search .......... 607/115–128
See application file for complete search history.

(56) References Cited

U.S. PATENT DOCUMENTS

| | | | |
|---|---|---|---|
| 4,764,132 A * | 8/1988 | Stutz, Jr. ..................... | 607/116 |
| 6,018,683 A | 1/2000 | Verness et al. | |
| 6,687,550 B1 * | 2/2004 | Doan ......................... | 607/127 |
| 6,704,605 B2 | 3/2004 | Soltis et al. | |
| 2002/0188340 A1 | 12/2002 | Bischoff et al. | |
| 2003/0144722 A1 | 7/2003 | Soltis et al. | |
| 2003/0195602 A1 * | 10/2003 | Boling ....................... | 607/122 |

OTHER PUBLICATIONS

German Search Report, issue by the German Patent Office on May 16, 2006 for patent application serial No. DE 10 2005 042 369.8.

* cited by examiner

*Primary Examiner*—Mark W Bockelman
*Assistant Examiner*—Roland Dinga
(74) *Attorney, Agent, or Firm*—Craig A. Fieschko, Esq.; DeWitt Ross & Stevens S.C.

(57) ABSTRACT

A screw-in electrode probe for cardiological application comprises an oblong electrode body (1), a supply line (10) running therein, and an electrode head (3) on the distal end (2). The latter is provided with housing (5), a shaft (6) mounted therein so it is rotatable and axially displaceable, and a corkscrew-like screw-in electrode (4) on the shaft (6). A contact spring in the form of an essentially planar spiral spring (11) is situated between these components, whose leg ends (12, 13) are in sliding contact with the housing (5) or the shaft (6), respectively, while exerting a radially directed spring force (F).

24 Claims, 1 Drawing Sheet

US 7,599,747 B2

SCREW-IN ELECTRODE PROBE FOR CARDIOLOGOCAL APPLICATION

FIELD OF THE INVENTION

The present invention relates to a screw-in electrode probe for cardiological application.

BACKGROUND OF THE INVENTION

Screw-in electrode probes are known from public prior uses or may also be inferred from US 2002/0188340 A1 or US 2003/0144722 A1. They have an oblong electrode body made of an electrically insulating material, a rotatable electric supply line running in the electrode body, and an electrode head situated at the distal end of the electrode body. The latter is provided with the housing from which a corkscrew-like screw-in electrode may be screwed into cardiac tissue through rotation around its coil axis with corresponding axial displacement. For this purpose, the screw-in electrode is seated coaxially on a shaft which is in turn connected in its axial extension to the supply line for the electrode—typically a coiled wire—running in the electrode body. A torque may be transmitted to the shaft via the supply line, through a corresponding pitch provider, the shaft is then rotated around its longitudinal axis and axially displaced in order to screw the screw-in electrode actively into the cardiac tissue or retrieve it therefrom again.

Depending on the application, it may be necessary, for reasons of signal or stimulation technology, to produce an electrical connection between the electrically conductive housing, which is made of metal, and the screw-in electrode itself, so that both elements are at the same electrical potential. This is typically implemented by a contact spring, for which different embodiments and installation possibilities are known through public prior use. It is to be ensured in principle in connection with the active fixing and the rotation of the screw-in electrode, with its shaft, and the simultaneous axial displacement connected thereto that the contact spring is also capable of compensating for radial displacements in addition to the axial movement of shaft and screw-in electrode. For this purpose, welding both ends of a type of clock spring, as is used for the balance wheel of a clock, for example, to the shaft and/or the housing is known. Because of the filigree configuration of this spring, this assembly step is relatively complex and sensitive in regard to the reliability of the contact connections. Furthermore, this type of spring requires a relatively large installation space, since the displacement path, which must cover the fixed connection points of the clock spring on the housing and shaft in relation to one another, is comparatively large, specifically two rotations at an axial displacement of 2 mm, for example. This path must be provided by the length of the spring leg without building up a noticeable counter tension during the rotation and axial displacement of the screw-in electrode.

A further known possibility is to use a coiled compression spring between the housing and a corresponding stop on the shaft or screw-in electrode. A system of this type requires a relatively large installation space in the axial direction, however. Furthermore, the spring force of the coiled compression spring counteracts the insertion of the screw-in electrode when it is actively withdrawn into the housing, which obstructs the electrode actuation.

Finally, using a type of torsion spring between the electrode shaft and the housing for the connection has already been attempted. Because of the small installation space available and the corresponding filigree dimensioning, this contact spring only has a very slight contact force, however, so that contact stability may not be ensured, particularly with the radial oscillations of the coil typical for screw-in electrodes.

SUMMARY OF THE INVENTION

Proceeding from the problems described above, the present invention is based on the object of improving a screw-in electrode probe in regard to its contact spring for the electrical connection between housing and electrode shaft in such a way that a reliable contact connection is ensured with a low space requirement of the contact spring.

This object may be achieved by configuring the contact spring as an essentially planar spiral spring rotating around the shaft under spring tension, whose leg ends are in sliding contact with the housing or the shaft while exerting a radially directed spring force.

Through the spiral embodiment of the contact spring rotating around the shaft, in spite of a compact construction, the effective spring length is significantly increased, through which a flatter spring characteristic is achievable with harder tuning of the spring. This provides the spring with a high distance tolerance in regard to both axial and also rotational movements of the shaft of the screw-in electrode. Since at least one of the leg ends, preferably both, are each in sliding contact, i.e., without permanent fixing in the form of welding or soldering, to the housing and/or the shaft, the contact spring does not also have to perform the rotational and axial displacement of the shaft for screwing in the electrode. Therefore, it does not need to provide any overall length for this purpose. The flat spring characteristic already noted above, which is thus possible, together with the very great length in relation to the prior art with minimum axial extension, ensures uniform contact forces with low tendency to inclination, even in the event of wobbling of the electrode shaft, which occurs regularly because of the tolerances in the electrode head.

Further advantages, features, and objects of the invention will be apparent from the following description of an exemplary embodiment of the invention in conjunction with the associated drawings.

DETAILED DESCRIPTION OF PREFERRED VERSIONS OF THE INVENTION

Figure 1:
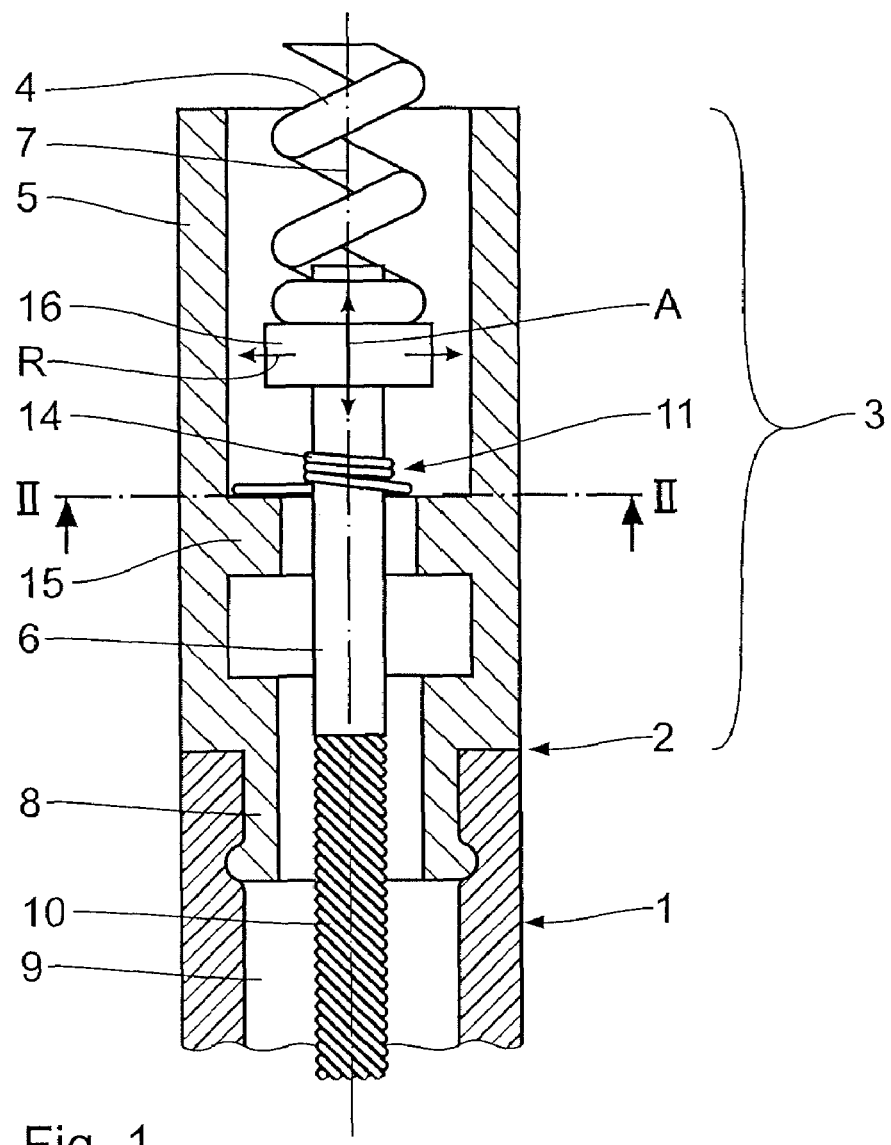
FIG. 1 shows a schematic axial section through the electrode head of a screw-in electrode probe.

As shown in FIG. 1 in particular, a screw-in electrode for cardiological application has an oblong, tubular electrode body 1 made of an electrically insulating material. Various supply lines to electrodes (not shown in greater detail), such as the ring electrodes at a distance to the distal end 2 of the probe, are housed therein.

At the distal end 2 of the electrode body 1 itself, an electrode head, identified as a whole by 3, is provided, which has a corkscrew-like screw-in electrode 4 which may be anchored in cardiac tissue. This electrode is rotatable in an essentially cylindrical housing 5 on a shaft 6 around its coil axis 7 and is mounted so it is axially displaceable in this direction. A bush 8 is provided on the housing 5 for connecting the electrode body 1 to the housing 5, onto which the lumen 9 of the electrode body 1 is pushed and fixed in a suitable way there. A conduction coil 10, which is permanently mechanically and electrically connected to the shaft 6, is guided in this lumen 9 of the electrode body 1 from the proximal end of the electrode probe. Via the conduction coil 10, electrical pulses may be guided for delivery via the screw-in electrode 4 or electrocardiological measuring signals may be guided from the screw-in electrode 4. In addition, the conduction coil 10 is so torsion-proof that a torque may be transmitted via it from the proximal end of the electrode probe to the shaft 6 for its rotation around the coil axis 7. The axial advance of the screw-in electrode 4 is caused via a pitch provider, which is integrated in the housing 5 but is not shown separately here.

Figure 2:
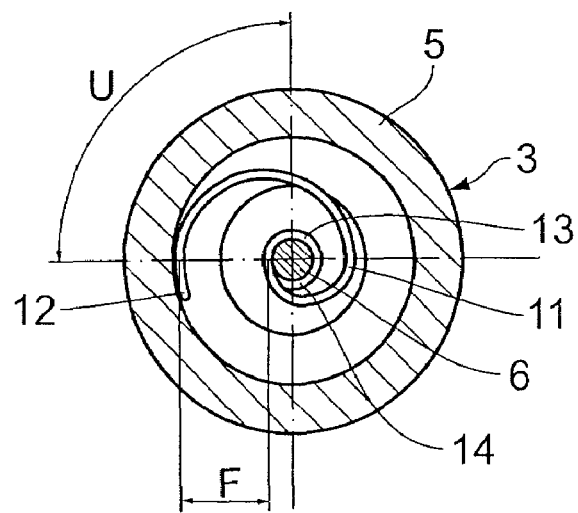
FIG. 2 shows a section along section line II/II in FIG. 1.

A contact spring, which is implemented as an essentially planar spiral spring 11, is provided to produce an electrical contact between the assembly made of screw-in electrode 4 and shaft 6 with the housing 5. The plane of extension of this spiral spring 11 is directed orthogonally to the coil axis 7, so that the leg ends 12, 13 of the spiral spring 11 are each supported at approximately the same height on the inner wall of the housing 5 and the lateral surface of the shaft 6, respectively. There is no rigid connection between the leg ends 12, 13 and the above-mentioned components of the electrode head, so that a sliding contact exists between spiral spring 11 and shaft 6 or housing 5, respectively. As may be seen from FIG. 2, the leg length of the spiral spring 11 is dimensioned in such way that it rotates around the shaft 6 under radial tension, the wrap angle U being at least 360°, preferably—as shown here—approximately 450°, however. Because of the system shown and described, both leg ends 12, 13 of the spiral spring 11 exert a spreading force F, which ensures a clean contact connection between the elements connected thereto. Therefore, both the axial displacement A of the screw-in electrode 4 using shaft 6 during anchoring and also radial play R occurring in this case may be compensated for without impairing the spring force F and thus the contact provided between the connected elements.

To support the contact provided between spiral spring 11 and shaft 6, an extension 14, like a coiled spring, is also provided on the inner leg end 13, which encloses the shaft 6 with play using two to three windings wound on a block. Furthermore, the spiral spring 11 is seated between an annular step 15 on the interior of the housing 5 and an annular shoulder 16 on the shaft 6. The screw-in electrode 4 is also seated on this annular shoulder 16 on the side facing away from the spiral spring 11.

The contact spring itself comprises a spring steel wire, for example. The contact spring preferably comprises platinum or a platinum alloy. The platinum alloy contains approximately 70 to 80% platinum, the remainder to 100% is made of iridium. The diameter of the wire is between 0.08 mm and 0.2 mm, the diameter of the wire is especially preferably 0.1 mm

What is claimed is:

1. A screw-in electrode probe for cardiological application comprising:
   a. an elongated electrode body made of an electrically insulating material, the electrode body having a distal end;
   b. an electrical supply line rotatably extending within the electrode body; and
   c. an electrode head on the distal end of the electrode body, the electrode head including:
      (1) a housing,
      (2) an electrically conductive shaft affixed to the supply line, the shaft being rotatably and axially displaceably mounted within the housing;
      (3) a screw-in electrode on the shaft, and
      (4) a contact spring extending between and electrically connecting the housing and the shaft, the contact spring being an essentially planar spiral spring wound around the shaft and exerting radially-oriented spring force, and having at least one of its outer and inner diameters in sliding contact with at least one of the housing and the shaft.

2. The screw-in electrode probe of claim 1 wherein the contact spring has a wrap angle around the shaft of at least 360°.

3. The screw-in electrode probe of claim 1 wherein the contact spring has a wrap angle around the shaft of approximately 450°.

4. The screw-in electrode probe of claim 1 wherein both the outer and inner diameters of the contact spring are in sliding contact with the housing and the shaft, respectively.

5. The screw-in electrode probe of claim 1 further comprising an extension from the planar spiral spring, the extension being defined by multiple coils wound about the shaft and extending from the inner diameter of the contact spring.

6. The screw-in electrode probe of claim 5 wherein the extension encloses the shaft with play.

7. The screw-in electrode probe of claim 1 wherein one portion of the length of the contact spring orbits another portion of the length of the contact spring.

8. The screw-in electrode probe of claim 1 wherein:
   a. the contact spring extends in an axial direction between a proximal spring end and a distal spring end, and
   b. only one of the proximal spring end and the distal spring end abuts one of more of the shaft and the housing.

9. The screw-in electrode probe of claim 1 wherein the spring is not compressible in the axial direction.

10. A screw-in electrode probe for cardiological application comprising:
    a. an electrode body made of an electrically insulating material, the electrode body having a distal end;
    b. an electrode head including:
       (1) an electrically conductive housing adjacent the distal end of the electrode body;
       (2) an electrically conductive shaft extending within the housing;
       (3) a screw-in electrode connected to the shaft; and
       (4) an electrically conductive contact spring extending between the housing and the shaft, the contact spring including an at least substantially planar spiral spring having an inner diameter wound around the shaft and an outer diameter contacting the housing.

11. The screw-in electrode probe of claim 10 wherein the spiral spring includes at least one full turn orbiting the shaft wherein this turn:
    a. is between the inner diameter and the outer diameter, and
    b. has a changing distance from the shaft and the housing over the length of the turn.

12. The screw-in electrode probe of claim 10 wherein the contact spring further includes an extension from the inner diameter of the spiral spring, the extension:
    a. extending axially adjacent the shaft and housing and
    b. being wound about the shaft with constant distance from the shaft.

13. The screw-in electrode probe of claim 10 wherein the inner diameter of the contact spring is slidable along the shaft.

14. The screw-in electrode probe of claim 10 wherein the outer diameter of the contact spring is slidable along the housing.

15. The screw-in electrode probe of claim 10 wherein one portion of the length of the contact spring orbits another portion of the length of the contact spring.

16. The screw-in electrode probe of claim 10 wherein:
   a. the contact spring extends in an axial direction between a proximal spring end and a distal spring end, and
   b. only one of the proximal spring end and the distal spring end abuts one of more of the shaft and the housing.

17. The screw-in electrode probe of claim 10 wherein the spring is not compressible in the axial direction.

18. A screw-in electrode probe for cardiological application comprising:
   a. an electrically conductive housing, the housing being at least substantially cylindrical with an axially-extending passage therein;
   b. an electrically conductive shaft extending within the housing passage, the shaft terminating in a screw-in electrode;
   c. an electrically conductive contact spring including:
      (1) an at least substantially planar spiral portion extending between the housing and the shaft, the spiral portion having an inner diameter contacting the shaft and an outer diameter contacting the housing;
      (2) an extension portion extending from the spiral portion, the extension portion including at least one turn about the shaft.

19. The screw-in electrode probe of claim 18 wherein the contact spring is slidable along the shaft.

20. The screw-in electrode probe of claim 19 wherein the contact spring is slidable along the housing.

21. The screw-in electrode probe of claim 18 wherein:
   a. the spiral portion is defined by a first length of spring which increases in radial distance from the shaft along the first length; and
   b. the extension portion is defined by a second length of spring which has at least substantially constant radial distance from the shaft along the length.

22. The screw-in electrode probe of claim 21 wherein the spiral portion abuts the housing.

23. The screw-in electrode probe of claim 18 wherein:
   a. the contact spring extends in an axial direction between a proximal spring end and a distal spring end, and
   b. only one of the proximal spring end and the distal spring end abuts one of more of the shaft and the housing.

24. The screw-in electrode probe of claim 18 wherein the spring is not compressible in the axial direction.

\* \* \* \* \*